US008893596B2

(12) United States Patent
Gil et al.

(10) Patent No.: US 8,893,596 B2
(45) Date of Patent: *Nov. 25, 2014

(54) OSTEOCHONDRAL PLUG GRAFT TRIMMING DEVICE AND METHOD

(75) Inventors: Carlos E. Gil, Collierville, TN (US); Daniel Andrew Shimko, Germantown, TN (US); Jeetendra Subhash Bharadwaj, Memphis, TN (US); Eric D. Weeks, Millington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 163 days.

This patent is subject to a terminal disclaimer.

(21) Appl. No.: 13/032,289

(22) Filed: Feb. 22, 2011

(65) Prior Publication Data

US 2011/0144648 A1     Jun. 16, 2011

Related U.S. Application Data

(62) Division of application No. 11/393,717, filed on Mar. 31, 2006, now Pat. No. 7,955,335, and a division of application No. 11/382,278, filed on May 9, 2006, now Pat. No. 7,997,174.

(51) Int. Cl.
| | |
|---|---|
| B26D 5/08 | (2006.01) |
| A61B 17/00 | (2006.01) |
| A61B 17/32 | (2006.01) |
| A61F 2/46 | (2006.01) |
| A61B 17/16 | (2006.01) |

(52) U.S. Cl.
CPC ........... *A61B 17/1635* (2013.01); *A61F 2/4644* (2013.01)
USPC ....... 83/13; 83/549; 83/618; 606/79; 606/167

(58) Field of Classification Search
USPC .......... 83/549–551, 553, 552; 606/79, 80, 81, 606/82, 83, 84, 85, 86, 167, 169, 170, 179, 606/180; 30/113.1, 114
See application file for complete search history.

(56) References Cited

U.S. PATENT DOCUMENTS

| | | | | | |
|---|---|---|---|---|---|
| 2,815,056 | A | * | 12/1957 | Gimelli | ......................... 241/262 |
| 3,292,257 | A | * | 12/1966 | Popeil | ............................. 30/301 |
| 3,403,442 | A | * | 10/1968 | Reese et al. | ................ 30/164.95 |
| 4,018,228 | A | | 4/1977 | Goosen | |
| 4,029,319 | A | * | 6/1977 | Christen | ....................... 473/584 |
| 4,062,260 | A | * | 12/1977 | Steinhogl | ..................... 83/404.3 |
| 4,134,205 | A | * | 1/1979 | Heling | ............................ 30/287 |
| 4,559,936 | A | * | 12/1985 | Hill | ................................. 606/79 |
| 5,195,413 | A | | 3/1993 | Johnson | |
| 5,904,232 | A | | 5/1999 | Shen | |

(Continued)

FOREIGN PATENT DOCUMENTS

WO         03071957 A2    9/2003

*Primary Examiner* — Ghassem Alie
*Assistant Examiner* — Bharat C Patel
(74) *Attorney, Agent, or Firm* — Sorell Lenna & Schmidt LLP (57) ABSTRACT

A device for trimming an osteochondral plug graft to an implantable configuration, includes a blade assembly terminating in a configured leading cutting blade and a plug graft housing comprising a substantially longitudinal holding sleeve having a bore and oriented complementarily to the longitudinal structure of the blade assembly to receive the longitudinal structure within the sleeve bore with the assembly cutting blade in close tolerance along an inner bore surface of the longitudinal housing structure.

19 Claims, 8 Drawing Sheets

(56) References Cited

U.S. PATENT DOCUMENTS

| | | | |
|---|---|---|---|
| 6,458,144 B1 * | 10/2002 | Morris et al. | 606/179 |
| 6,689,147 B1 | 2/2004 | Koster, Jr. | |
| 6,695,867 B2 * | 2/2004 | Ginn et al. | 606/213 |
| 6,749,621 B2 * | 6/2004 | Pantages et al. | 606/213 |
| 6,962,592 B2 | 11/2005 | Gatturna et al. | |
| 7,427,293 B2 | 9/2008 | Nycz et al. | |
| 7,934,317 B2 * | 5/2011 | Chiu | 30/102 |
| 7,955,335 B2 * | 6/2011 | Gil et al. | 606/79 |
| 7,997,174 B2 * | 8/2011 | Gil et al. | 83/13 |
| 2001/0029387 A1 | 10/2001 | Wolf et al. | |
| 2004/0049198 A1 | 3/2004 | Gatturna et al. | |

* cited by examiner

OSTEOCHONDRAL PLUG GRAFT TRIMMING DEVICE AND METHOD

CROSS-REFERENCE TO RELATED APPLICATIONS

This application is a divisional application of U.S. application Ser. No. 11/393,717, filed Mar. 31, 2006, now U.S. Pat. No. 7,955,335, and U.S. application Ser. No. 11/382,278, now U.S. Pat. No. 7,997,174, filed May 9, 2006.

BACKGROUND OF THE INVENTION

This invention relates to an osteochondral plug graft trimming device and method.

Human joint surfaces are covered by articular cartilage that provides a resilient, durable surface with low friction. Cartilage is an avascular tissue that has a small number of chondrocytes encapsulated within an extensive extracellular matrix. The cartilage acts to distribute mechanical forces and to protect subchondral bone. The knee is a particular instance of a cartilage surfaced (the condyle) bone area. The knee comprises three bones—the femur, tibia, and patella that are held in place by various ligaments. Corresponding chondral areas of the femur and the tibia form a hinge joint and the patella protects the joint. Portions of the chondral areas as well as the underside of the patella are covered with an articular cartilage that allows the femur and the tibia to smoothly glide against each other without causing damage.

Damage to the articular cartilage, subchondral bone or both can result from traumatic injury or a disease state. For example, articular cartilage in the knee can tear due to traumatic injury as with athletes and degenerative processes as with older patients. The knee cartilage does not heal well due to lack of nerves, blood vessels and a lymphatic system. Hyaline cartilage in particular has a limited capacity for repair and lesions in this material without intervention, can form repair tissue lacking the biomechanical properties of normal cartilage.

A number of procedures are used to treat damaged articular cartilage. Currently, the most widely used procedure involves lavage, arthroscopic debridement and repair stimulation. Repair stimulation is conducted by drilling, abrasion arthroplasty or microfracture. The goal of this procedure is to penetrate into subchondral bone to induce bleeding and fibrin clot formation. This promotes initial repair. However, the resulting formed tissue is often fibrous in nature and lacks the durability of normal cartilage.

Osteochondral grafting has been used to repair chondral damage and to replace damaged articular cartilage and subchondral bone. First in this procedure, cartilage and bone tissue of a defect site are removed by routing to create a bore of a precise cylindrical geometry. Then a cylindrical cartilage and subchondral bone plug graft is harvested in a matching geometry. The harvest is typically from another body region of less strain. The plug graft can be harvested from a recipient source (autograft) or from another suitable human or other animal donor (allograft). The harvested plug graft is then implanted into the bore of the routed defect site. Healing of the graft bone to host bone results in fixation of the plug graft to surrounding host region.

Surface characteristics of the plug graft are critical. For a successful procedure, surface of the transplanted graft must have the same contour as the excised osteochondral tissue. If the contour is not a correct match, a repaired articular surface is at risk for further damage.

Also, osteochondral grafts are typically harvested in a cylindrical plug form. However, a cylindrical shape does not pack well into irregularly shaped defects. Further, cylindrical plug grafts have a propensity to rotate. This results in poor integration of the plug graft with surrounding host tissue.

There is a need for a device and method to overcome post implantation motion, graft surface mismatch and host tissue integration failure.

BRIEF DESCRIPTION OF THE INVENTION

The invention relates to a device and method that overcome host tissue integration failure and post implantation motion. In a first embodiment, the invention is a device for trimming an osteochondral plug graft to an implantable configuration, comprising: a longitudinal blade terminating in a configured leading cutting edge; and a substantially longitudinal plug graft holding sleeve having a bore and oriented to coaxially receive the longitudinal blade within the sleeve bore with the blade in close tolerance along an inner bore surface of the holding sleeve.

In another embodiment of the invention, a method for repairing articular cartilage in a patient comprises: loading an osteochondral plug graft into a longitudinal holding sleeve so that the plug graft is biased against a surface of the holding sleeve.

Another embodiment is a kit for a surgical procedure, comprising: a plurality of longitudinal cutting blades each terminating in a differently sized or configured leading cutting blade; and a longitudinal holding sleeve having a bore to receive a plug graft.

Another embodiment is a device for trimming an osteochondral plug graft to an implantable configuration, comprising: a housing with a housing through bore; a support altar with a pedestal partially extending within the housing through bore and terminating in a flat impact surface parallel to a traverse axis of the housing through bore; a guide slidably fitted to the housing and a guide through bore aligned with the housing through bore to form a continuous passageway; a plug holding sleeve nestled within the housing through bore to hold a plug graft in an shearable orientation aligned within the continuous passageway; and an integral adjustable assembly to access and pare the osteochondral plug graft to a selected configuration.

DETAILED DESCRIPTION OF THE INVENTION

An embodiment of the invention provides a device and method for trimming both cross section and length of an osteochondral plug graft. An allograft or autograft plug can be harvested in an oversize or random configuration and shipped oversized to a location of implanting such as to an operating room. At the operating room, the graft can be trimmed down to the appropriate size as needed for an osteochondral implantation by using the device and method of the invention. For example, a 16 mm side dimension round plug can be harvested from a donor and stored in a tissue bank. Then at an operating room, the plug can be trimmed an 8 mm, 10 mm or 12 mm, round or square shape, as appropriate for an instant implanting.

A feature of the invention is to use an apparatus that is somewhat like a matched punch and die set with a support for the to-be-shaped material. This particular type of apparatus is appropriate for cutting the very particular physical characteristics of purified allograft bone. In the invention, the length of an osteochondral graft that has a cartilage portion overlying an end of a condyle portion can be trimmed to a size for implanting in a patient. For example, a graft as initially received is approximately 20 millimeters in length. It is desired to cut the plug to 10 millimeters in length and 10 millimeters in width to correspond to a configuration of a recipient socket formed in a patients defect area.

One trimming device according to the invention comprises a stationary altar-shaped base, a housing, an impactor and an upper guide with a horizontal upper plate. The housing includes a horizontal base plate and the impactor includes an upper cutting plate. The housing can include a bore and at least two vertical receivers. The guide can include at least two posts complementary to the receivers for connecting the guide to the housing. A sleeve has the same cross section as the housing bore so that it can sit inside the bore. The top surface of the sleeve is flat and the top surface and that of the housing outboard of the opening are substantially flush.

The invention advantageously provides an increase in supply of available osteochondral plug grafts by providing a device and method to use customizable and storable grafts. The invention reduces operating room time for perpendicular walled trimming. The plugs can be trimmed to an appropriate length and an appropriate cross section with a minimum handling of the plug.

Features of the invention will become apparent from the drawings and following detailed discussion, which by way of example without limitation describe preferred embodiments of the invention.

A First Instrument Embodiment

Figures 1, 3:
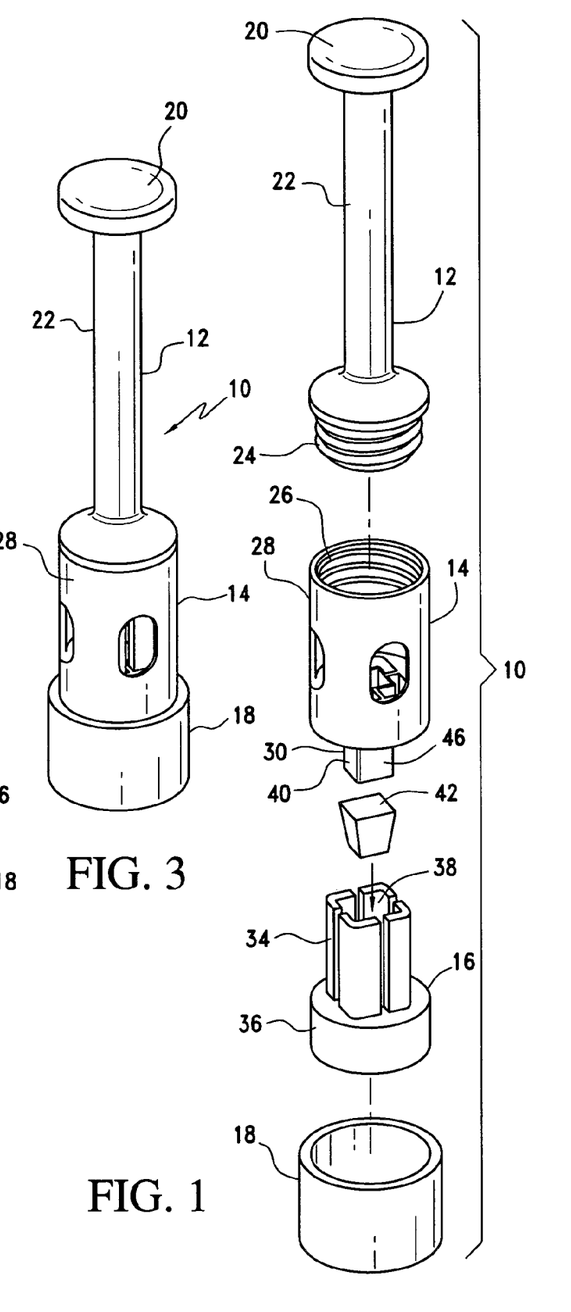
FIG. 1 is a perspective, exploded view of a first device of the invention.
FIG. 2 and FIG. 3 are perspective views of the device of FIG. 1.
Figure 2:
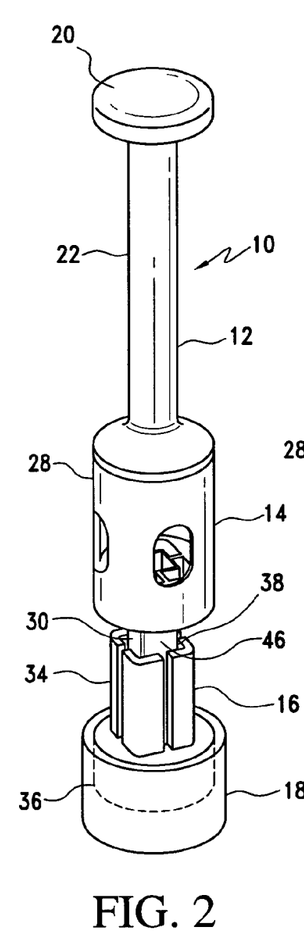

FIGS. 1 to 6 show a preferred plug graft trimmer 10. FIG. 1 is an exploded perspective view of graft trimmer 10, FIG. 2. is a perspective view of the trimmer 10 in a poised position and FIG. 3 is a perspective view of the trimmer 10 in an impacted position. The FIGS. 1 to 3 show impactor 12, blade assembly 14, plug graft housing 16 and housing sleeve 18.

In the FIGS. 1 to 6, impactor 12 includes handle surface 20 and stem 22 and thread 24. Thread 24 has complementary threaded fit to inner thread 26 within inner blade sleeve 28 of blade assembly 14. Blade assembly further includes blade 30 that extends from lower base 32 of the blade assembly 14. Plug graft housing 16 includes plug holding sleeve 34 and base 36.

In a procedure upon arrival of osteochondral plug graft 42 from a tissue bank or directly from a donor, it is loaded into plug holding sleeve 34 of plug graft housing 16 as illustrated in FIG. 1. A sized plug holding sleeve 34 is selected to hold the loaded osteochondral plug graft 38 in a snug relationship, biased against inside faces 38 of the holding sleeve 34. In the embodiment shown, a vertically slotted plug holding sleeve 34 provides a suitable biased fit against inside faces 38 to facilitate paring of the osteochondral plug graft as hereinafter described. It should be noted that the osteochondral plug graft 38 is illustrated as a trapezoid figure with a square cross-section. However, the osteochondral plug graft 38 can be any three dimensional configuration including but not limited to a cylinder, cube, trapezoid and a truncated prism or cylinder. Similarly, the blade 30 and plug holding sleeve 34 can be selected from a plurality of configurations and sizes to facilitate the shaping of any desired implantable plug graft. For example, if an osteochondral plug recipient socket in a patient is so configured as to admit of a cylindrical plug graft, then blade 30 and plug holding sleeve 34 can be selected to provide an appropriate cylindrical implantable plug graft.

Figures 4, 5:
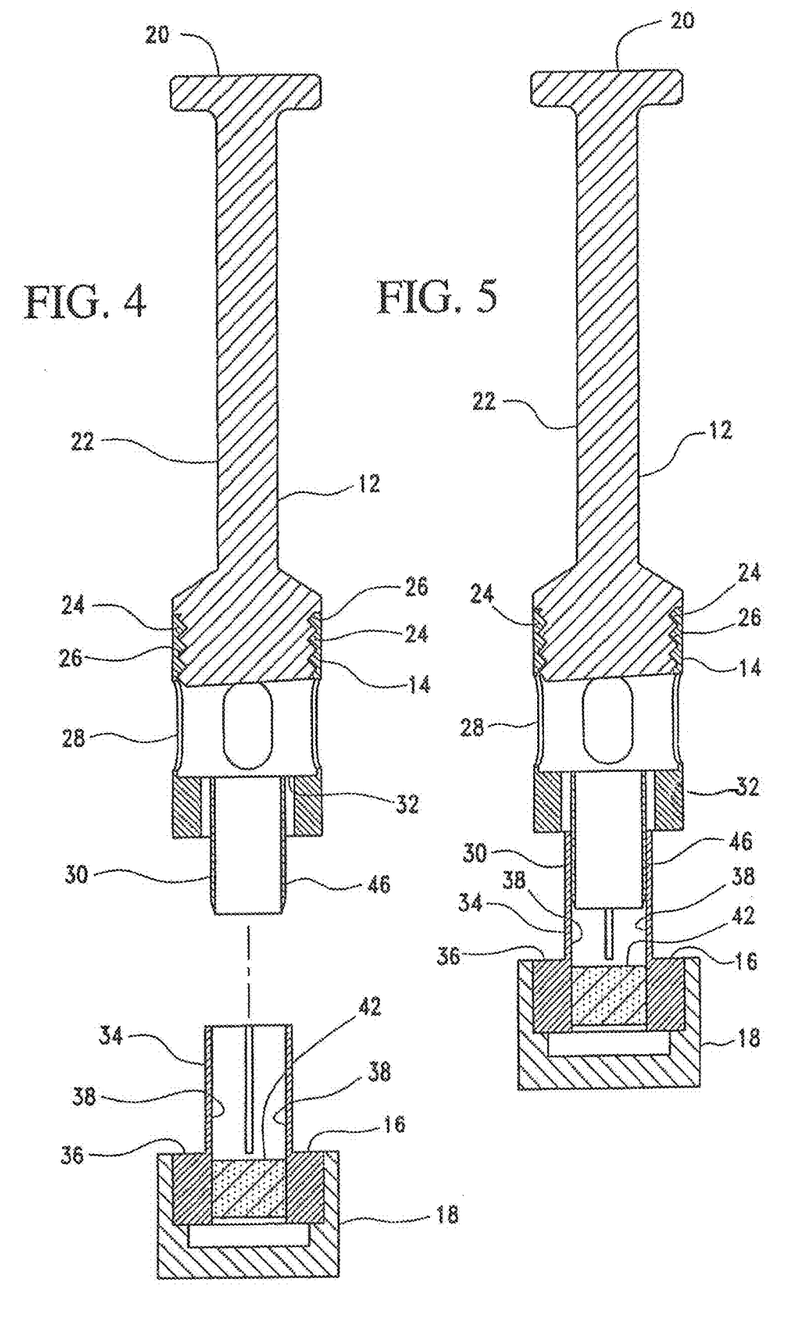
FIG. 4, FIG. 5 and FIG. 6 are cut away side elevations of the FIG. 1 device.

After emplacement of the osteochondral plug graft 42 within the plug holding sleeve 34, the plug graft housing 16 is placed within housing sleeve 18 as shown in FIG. 2 and FIG. 4. Impactor 12 is threaded to blade assembly 14 via threads 24 and 26. The threaded impactor 12 and blade assembly 14 are placed over plug graft housing 16 within housing sleeve 18 as illustrated in FIGS. 2 to 6. As the threaded impactor 12 and blade assembly 14 are emplaced, inside faces 38 of plug holding sleeve 34 guide outside surfaces 40, 46 of blade 30 through a height of the blade 30 to rest on top of the osteochondral plug graft 42. Then a force is applied to handle surface 20 of the impactor 12 either by manual force or by impact of a tool such as a mallet, to drive the impactor and correspondingly the threaded blade assembly 14 substantially along side the inside surfaces 38 of the plug holding sleeve 34. As noted above, plug holding sleeve 34 is size to hold the loaded osteochondral plug graft 42 in a snug relationship, constrained against inside faces 38 of the holding sleeve 34. By constrained is meant that the graft 42 is held by an imposed stricture of the faces 38. Hence, as the blade 30 is impacted downwardly against biased osteochondral plug graft 42, the beveled cutting edge of blade 30 passes along the graft 42 in a shearing manner to pare the surface of the graft 42 to a desired size. "Pare" in this application means to diminish or reduce by shaving or trimming a thin slice of osteochondral plug graft close to its surface.

Figure 6:
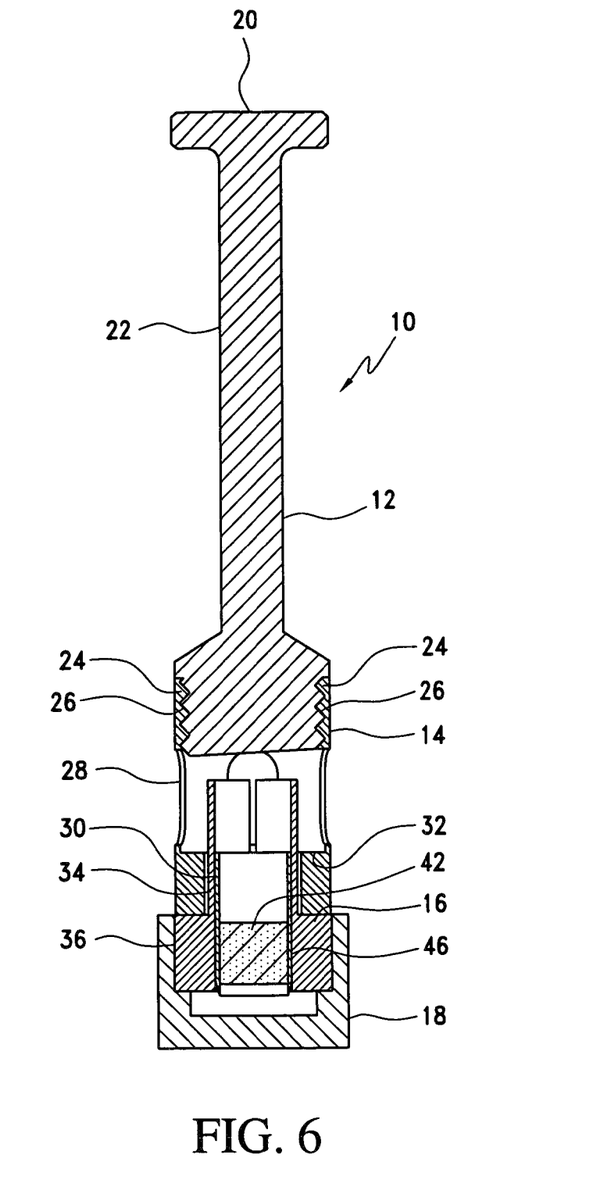

After the blade 30 has been impacted through the osteochondral plug surface as shown in FIG. 6, the blade assembly 14 is withdrawn from the housing sleeve 18 and is disassembled from impactor 12. The pared osteochondral plug graft 38 is ejected from the blade 30 by pushing on the graft 38. The plug 38 is now sized and configured for implanting into a recipient socket of a patient.

A Second Instrument Embodiment

Figure 7:
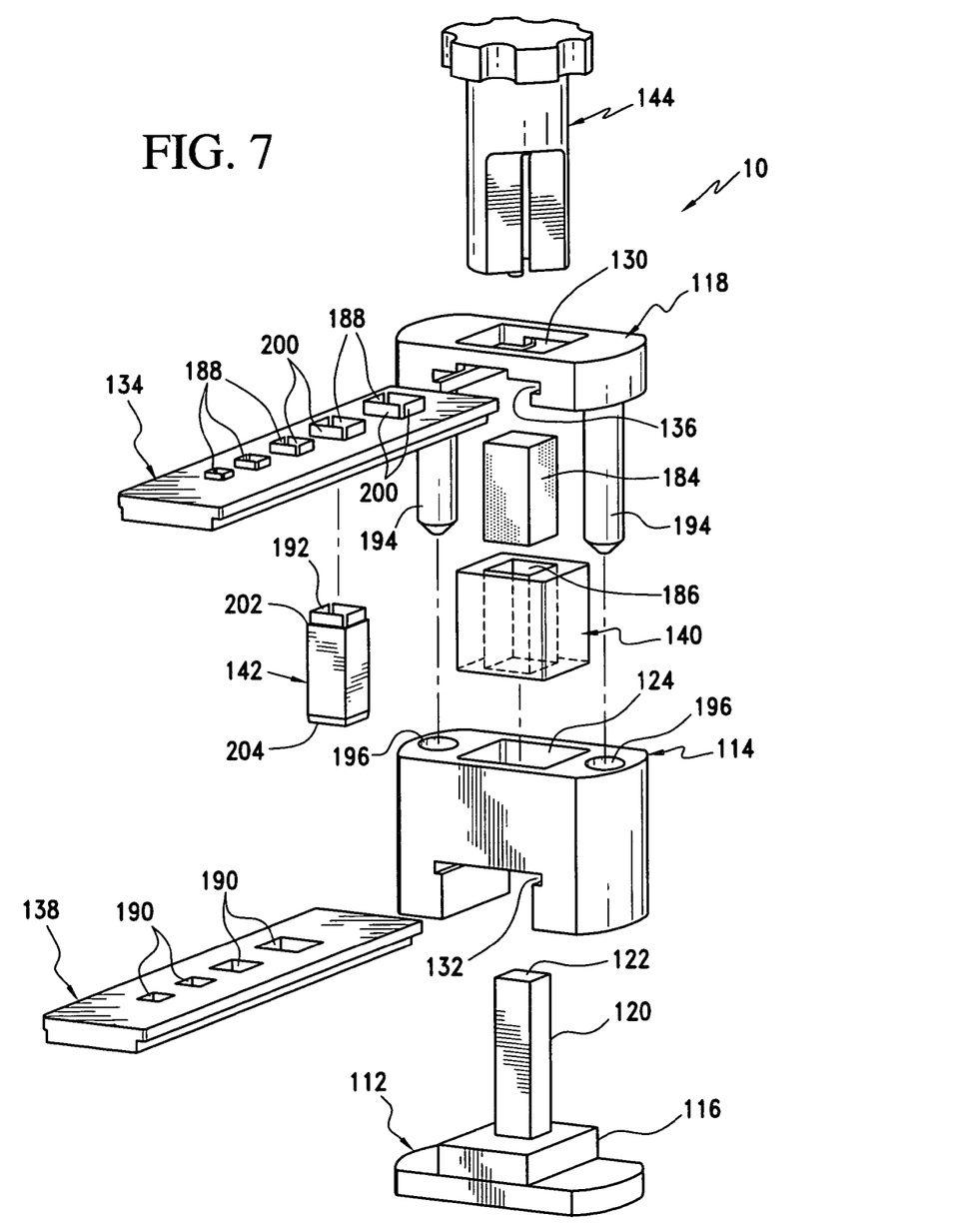
FIG. 7 is a perspective, exploded view of a second device of the invention.

FIG. 7 is an exploded perspective view of an adjustable osteochondral plug graft trimmer 110 according to a next preferred embodiment. The adjustable plug graft trimmer 110 comprises support altar 112, housing 114 supported on the base 116 of altar 112 and guide 118.

Figures 13, 14:
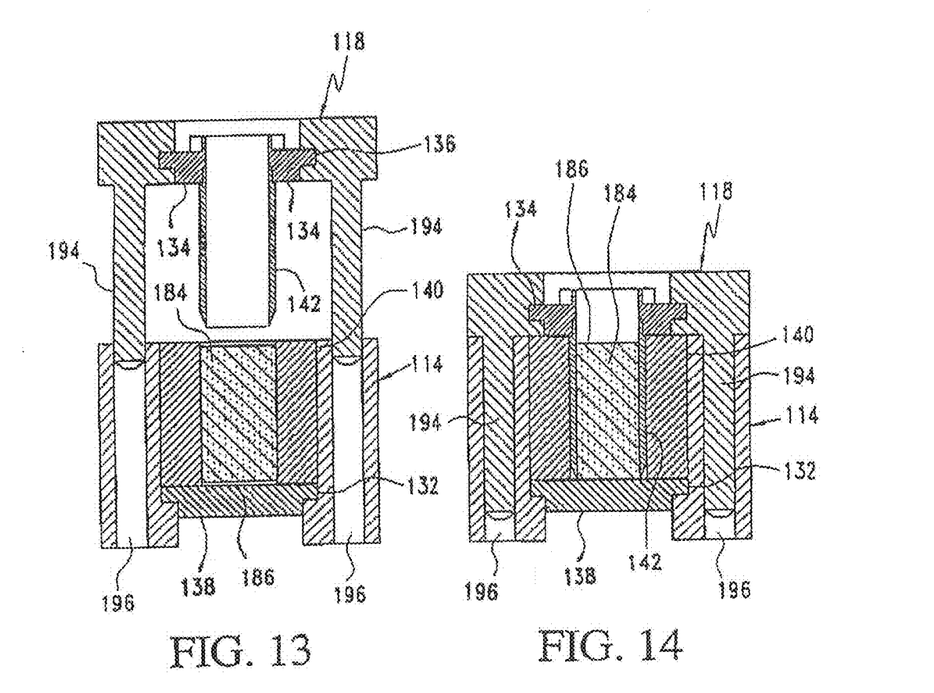
Figure 15:
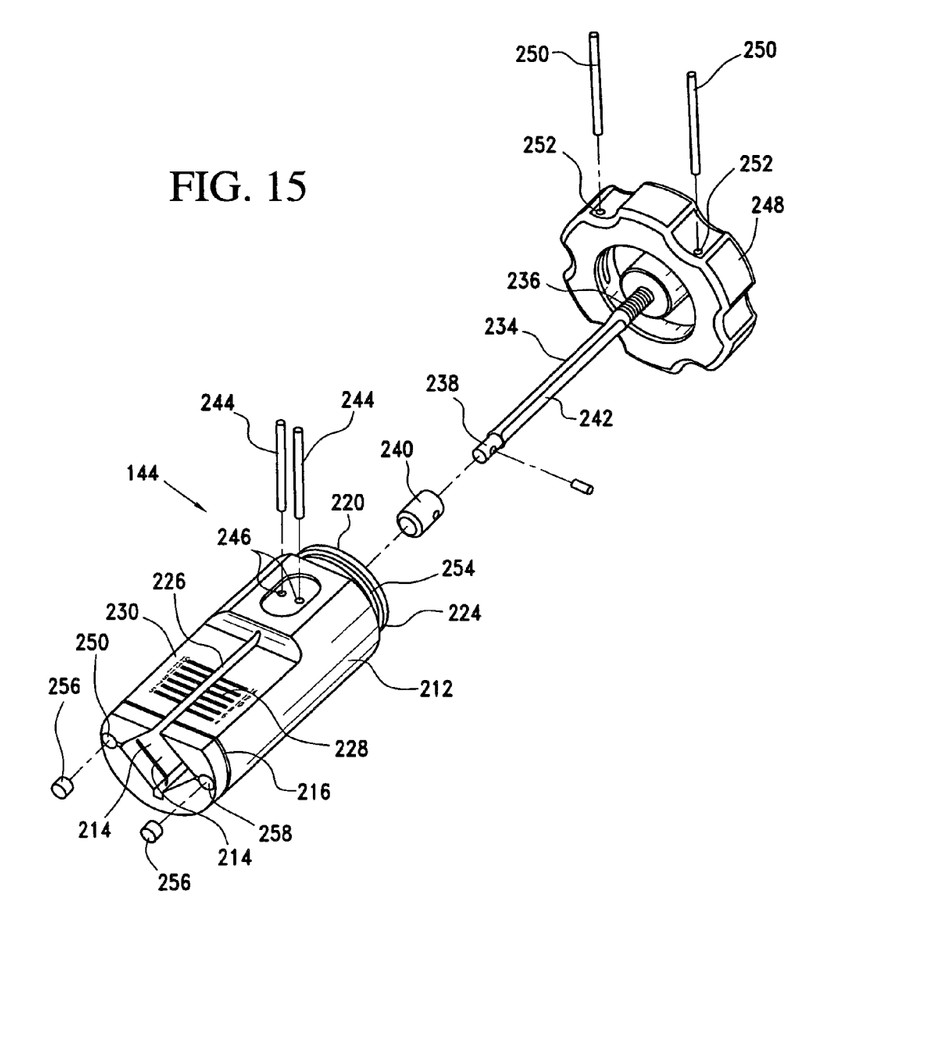
Figure 16:
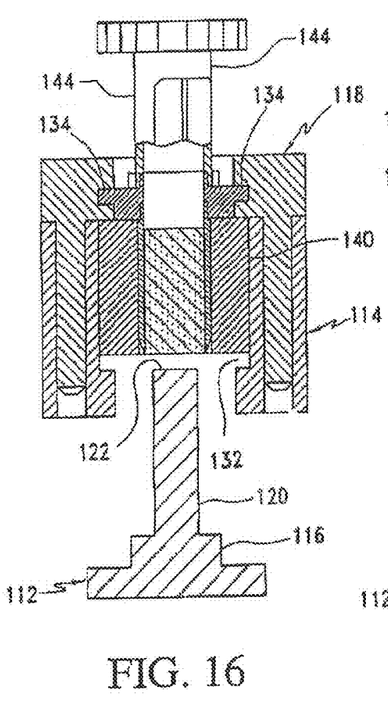
FIG. 16 and FIG. 17 are schematic cut away elevations of the FIG. 15 part in operation.

FIG. 13 and FIG. 14 are side elevation views showing mating of housing 114 to support altar 112 as hereinafter described. Referring to FIG. 7 and FIGS. 15 and 16, altar 12 includes base 116 and an elevating elongated pedestal 120. Elevated elongated pedestal 120 is vertically oriented from base 16 and terminates in a flat impact surface 122 at a distal end from the base 16.

Figures 8, 9, 10:
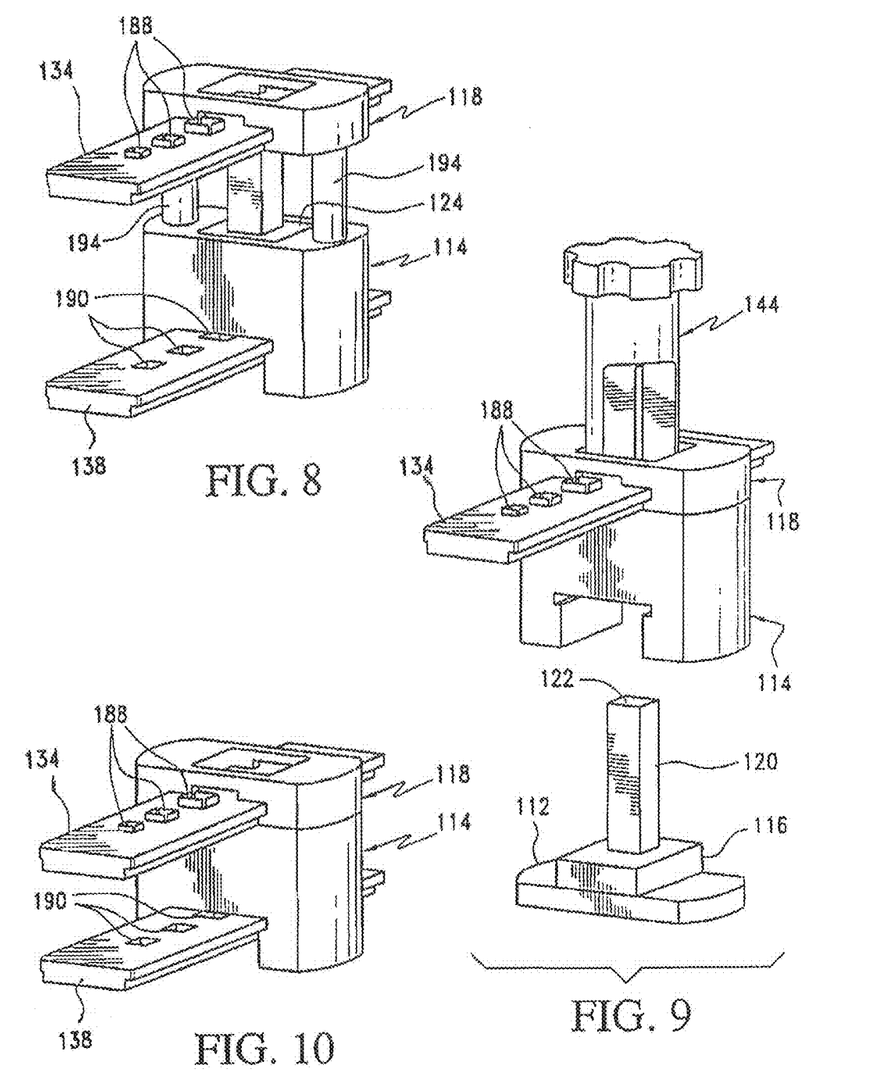
FIG. 8, FIG. 9, FIG. 10 and FIG. 15 are perspective views of parts of the device of FIG. 7.

In FIG. 7 and FIGS. 11 through 14, housing 114 comprises a structure that includes a bore 124 vertically traversing housing 114 and shaped to accommodate elongated pedestal 120 in a nested relationship within bore 124. Guide 118 is a bridge or table shaped structure with posts 194. Vertical sockets 128 of housing 114 are channels that receive complementary posts 194 of guide 118 as shown in FIG. 13 to form a fitting to secure housing 114 and guide 118 as shown in FIGS. 13 and 14. Guide 118 has a bore 130 that forms a continuous passageway with bore 124 of housing 114 when the guide 118 and housing 114 are secured to each other as shown in FIGS. 8, 9 and 10. FIG. 7 also shows an insertable base plate 134 and insertable base plate 138. Housing 114 has slot 132 that horizontally traverses through the bore 124 of the housing 114 for receiving base plate 138 and guide 118 has slot 136 that horizontally traverses through bore 130 for receiving blade plate 134 as hereinafter described.

Still further, FIG. 7 shows blade 142 and impactor 144. Blade 142 is shown as a single size but can be provided in a multiplicity of sizes to accommodate a selected implant size for a patient. Further, plug holding sleeve 140 is shown in FIG. 7, configured to nest into housing bore 124. Plug holding sleeve 140 comprises a rectangular shape channel 198 configured to receive a plug graft 184. While the "blank" plug graft is shown in a cylinder shape, the plug graft can be any useable shape including cubic, trapezoid, parallelogram and the like. Also, while the holding sleeve 140 is shown in this embodiment as having a square cross section so as to carve a square cross section plug graft, the holding sleeve can be any convenient shape in cross section including, round, oval, square and rectangle to form a corresponding cross sectional shaped plug graft implant. For example in a procedure, a plug graft 184 is harvested in a gross size and is delivered to a surgical site. For example, the plug graft 184 can be harvested in an 11.9 mm cross-section size. At the site, the plug graft 184 is positioned within holding sleeve 140 so that it is constrained against the sleeve 140 inner walls. A blade 142 is selected to pare a close tolerance surface from the plug graft 184 to provide a required implant size and configuration. For example, a blade can be selected of a size to pare 0.01 mm to 0.4 mm of cross section from the plug, desirably 0.10 mm to 0.3 and preferably 0.15 to 0.25 mm to provide an about 9.9 mm, 7.9 mm or 5.9 mm size for implanting.

Raised lips 200 are provided at boundaries of each opening 188 of the blade plate 134. Each blade 142 has corresponding extensions 202 the interface with lips of respective openings 188 when a blade 142 is inserted into a respectively sized opening 188 of the plate 134. These features permit firm attachment of a selected cutting blade 142 to the plate 134.

Together the arrangement of the channeled cutting blade 142, the holding sleeve 140 and the surrounding surface of the guide 118 provide a punch and die set type of functionality. The matched punch and die set analog of this invention comprises the channeled cutting blade 142, which mates slidably within the holding sleeve 140, which has a substantially identical cross section shape. An outer support is provided via the guide 118, which is shaped such that its bore 130 is substantially the same cross-section as that of the holding sleeve 140 but displaced uniformly outward such that the cutting blade 142 slides snugly but smoothly into and out of a space between the holding sleeve 140 and guide bore 130. The blade 142 can comprises leading beveled cutting edge 204 and in some embodiments, points, all with sharpened cutting edges configured so as to slice cleanly into a bone from which the implant is to be cut.

The holding sleeve located on the stationary base plate slidably receives the channeled blade 142 attached to the horizontal upper plate 134. In operation, a segment of bone to be shaped is placed within holding sleeve 140 and the sleeve is inserted into guide bore 130. Downward pressure is applied to the guide 118 so that the blade 142 is driven through a plug graft blank to form a dimension of the plug graft 184.

The combination of vertical guide posts 194 and complementary receivers 196 on the housing 114 function to keep the path traveled by the cutting blade 142 substantially parallel to a longitudinal axis of the holding sleeve 140, which in the preferred embodiment is vertical.

The channeled cutting blade 142, holding sleeve 140 and guide 118, collectively form a complementary cutting set that represents any number of different embodiment combinations sizes and configurations. Matched cutting sets of a cutting blades, for example with cylindrical shape, complementary cylindrical holding sleeve and guide with a central cylindrical cross sectional opening form a slot just the width of a channeled cylindrical blade, upon which a donor bone is placed. The channeled cylindrical cutting blade is forced through the donor bone and over the holding sleeve to form a cylindrical plug graft.

The sleeve 140 with the plug graft 184 is then placed in housing 114 with base plate 138 assembled into housing 114. Blade plate 134 is assembled to impact guide 118 and an appropriate sized blade 142 is attached to blade plate 134. Impact guide 118 along with blade plate 134 and blade 142 is then positioned with sleeve 140 over housing 114. A standard surgical hammer is applied to guide 118 to tap the guide 118 through the height of the housing 114 to cause blade 142 to shear along an outer plug graft surface of the constrained plug graft 184. The blade 142 pares the plug graft 184 to the selected first cross section size.

Impactor 144 is described in detail with reference to FIG. 7, FIG. 9 and FIG. 15. FIG. 7 and FIG. 9 show that impactor 144 can be fitted within guide bore 130 of guide 118 and driven with the guide 118 as the guide 118 is advanced along the housing receivers 196 into a conforming fit with housing 116. FIG. 15 is an exploded perspective detail of impactor 144. FIGS. 7, 9 and 15 depict impactor 144 for trimming a plug graft 184 harvested from an undamaged non-load bearing area of a patient or recipient or from a donor and sheared into a first dimension by blade 142. The impactor 144 comprises a cylindrically-shaped body member 212 having a continuous bore 214 formed for receiving the plug graft 184. Bore 214 has a rectangular cross-section that can correspond to a cross-section of a plug graft such as plug graft 184 One end of the bore 214 serves as an inlet for receiving the plug graft 184. A transverse cutting slot 216 extends through the body member 212 in a spaced relationship to inlet 218 for cutting the graft, in a manner to be described. An annular flange 220 extends from another end 222 (opposite the inlet 218 end) of the body member 212. A circumferential groove 224 is formed in the flange 220. An longitudinally extending slot 226 is formed through surfaces 230 of the body member 212, as viewed in the drawing.

Indicia 228 are provided as shown on surface 230 to either side of the slot 226. In the example shown in the drawings, the indicia 228 indicate distance in millimeters along slot 226. The indicia 228 provide part of a mechanism for adjusting a position of a plug graft 184 in bore 214. The mechanism includes rod 234 adapted to extend within bore 214. One end portion 236 of the rod 234 is externally threaded and another end 238 is adapted to be connected in any conventional manner, such as by a set screw to plunger 240. Outer surfaces 242 of two opposed side portions of rod 234 are flat, and two dowels 244 extend through complementary openings 246 in the body member 112 to engage flat surfaces 142 of rod 234 to prevent rotation of the rod 234 in the body member 212.

A knob 248 has an internally threaded bore (hidden) in threaded engagement with part of the threaded end portion 136 of the rod 234. Two dowels 250 extend through two transverse openings 252 formed in the knob 248 and into the groove 254. This secures the knob 248 against axial movement relative to the body member 212 while permitting rotational movement. A pair of magnets 256 is located in corresponding openings 258 formed in the end of the body member 212 adjacent an inlet 216 of the bore 214. The impactor 144 is shown perspective in an assembled condition in FIG. 15 with rod 234 and therefore the plunger 240, in fully extended position with the plunger 240 located at the inlet 216 of the bore 214.

Figure 11:
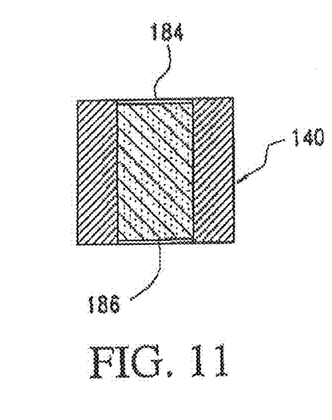
FIG. 11, FIG. 12, FIG. 13 and FIG. 14 are cut away side elevations of parts of the FIG. 1 device.
Figure 12:
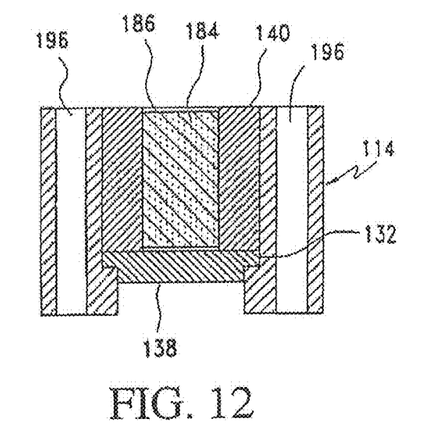

The impactor 144 can be used to configure a plug graft into an appropriately sized three dimension shape for implanting in a recipient socket in a condyle surface of a patient. In a procedure to use the adjustable plug trimmer 110, an oversized plug graft 184 is obtained from a tissue bank and is emplaced into the plug holding sleeve 140. FIGS. 11, 12, 13 and 14 are cut away elevation views illustrating placement and trimming of plug graft 184. FIG. 11 is a front elevation view, cut away to show plug holding sleeve 140 holding a plug graft 184 within its bore 186. FIGS. 12, 13 and 14 then show the sleeve 140 emplaced into housing 114 with an inserted base plate 138.

An appropriate sized blade 142 is selected and attached to the blade plate 134. The blade plate 134 with blade 142 is inserted to the impact guide 118 by means of the plate 134, as shown in FIG. 7 as well as perspective views FIGS. 8 to 10 and cut away views of FIGS. 13 and 14. The similarly aligned base plate 138 is emplaced within housing slot 132 as shown in FIGS. 7 to 3 and FIGS. 12 to 14. The plate 138 is inserted so that an opening 190 of the plate 138 that corresponds to the selected opening 188 of the blade plate 134 and bore 192 of blade 142 are all aligned with housing bore 124 to form a continuous passageway. The housing 114 is placed onto support altar 112 with elongated pedestal 120 extending upwardly within the bore 124 of the housing 114. The graft 184 is placed within plug holding sleeve 140 and the sleeve 140 with the graft 184 is placed onto face 122 of the elongated pedestal 120 within the housing bore 124. Elongated pedestal 120 of support altar 112 as the holding sleeve is advanced within housing 114 to a contact position with a plug graft postured on flat surface 122 of pedestal 120 as shown in FIGS. 15 and 16. Then, the impact guide 118 along with the blade plate 134 and blade 142 is impacted through the height of housing bore 124, for example by driving with a standard surgical mallet. The driving mates the impact guide 118 with the housing 114 by inserting posts 194 of the impact guide 118 into receivers 196 of the housing 114. Driving the blade through the housing bore 124 pares the plug graft 184 to a desired first cross-sectional dimension. Base plate 138 provides a "cutting board" type of function to stabilize a plug 184 for clean cleavage by an impacting blade 142. The plate 138 can be made of a relatively soft plastic material to avoid damage to the impacting blade 142. For example, the plate 138 can be made from Delrin® plastic, an acetal resin from E. I. du Pont de Nemours and Company Corporation Delaware, 1007 Market Street, Wilmington, Del. 19898. After shaping the plug 184 with the blade 142 in a first direction, the impact guide 118 is removed and a base plate opening 190 is aligned with the plug 184 permitting the pedestal 120 to push the plug from the blade 142 to impactor 144.

Figure 17:
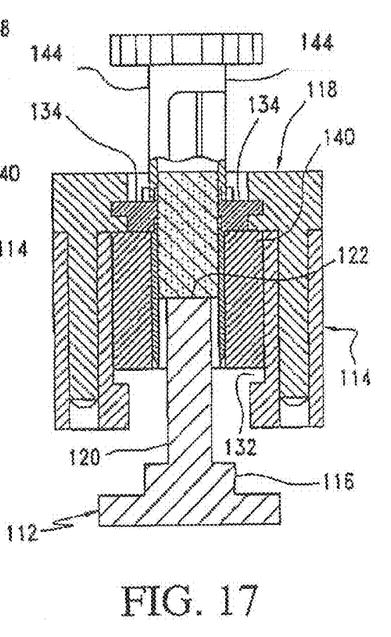

Before use, knob 248 of the impactor 144 is rotated in a direction to cause axial movement of rod 234 and therefore plunger 240 to a fully retracted position, i.e., a position in which the plunger 240 is a maximum distance away from the cutting slot 216. Then the cylindrically-shaped body member 212 of impactor 144 is inserted within the extending bore 130 of guide 118 as shown in FIG. 16 and FIG. 17. Referring to FIG. 16 and FIG. 17, body member 212 interfaces with the blade plate 134. Impactor 144 receives both the lips of openings 188 of plate 134 along with interfaced blade extensions 202 to seat the blade 142 end within bore 214. The combined structure of the impactor 144, plate 134 and blade 142 is imposed downwardly onto altar base 116 so that elongated pedestal 120 pushes the osteochondral plug 184 from the blade 142 bore 192 into the impactor 144.

The impactor 144 has length markings (indicia 228) and a cutting slot 216 for a surgical blade (not shown) to pass through the extracted plug 184. Knob 148 is rotated till a desired length reading is registered at the indicia 228. Then the length of then plug 184 is cut with the blade. Again, the knob 248 is rotated until plug 184 is pushed out of the impactor 144. The plug 184 is now of a selected cross section and selected length for implanting.

The invention provides a device to trim an osteochondral plug graft both in its length and cross section. The invention permits an allograft plug to be harvested in an oversize at a tissue bank and shipped to an operating room where it can be trimmed to an appropriate size as need for implantation to a patient. For example, a tissue bank can supply a square or round harvested osteochondral plug graft in a 16 mm dimension. At the operating room, the plug graft can be trimmed to a required 8 mm, 10 mm or 12 mm (square dimension or cylinder diameter) to fit a recipient socket in a patient.

While preferred embodiments of the invention have been described, the present invention is capable of variation and modification and therefore should not be limited to the precise details of the Examples. The invention includes changes and alterations that fall within the purview of the following claims.

What is claimed is:

1. A device for trimming an osteochondral plug graft to an implantable configuration, comprising:
    a housing with a housing through bore that forms a continuous passageway in the housing, said housing defining an impact guide configured to receive a blade plate assembly including a plurality of alternatively sized cutting blades positioned thereon, said blade plate assembly configured to slide into said impact guide to selectively align one of said alternatively sized cutting blades with said continuous passageway, the blade plate assembly including a plurality of alternatively sized openings, each of the openings having one of the cutting blades positioned therein, each of the openings having a raised lip at a boundary thereof;
    a selected longitudinal cutting blade of said blade plate assembly terminating in a configured leading cutting edge;
    an impactor connected to the blade plate assembly at an end opposite the leading cutting edge; and
    a substantially longitudinal plug graft holding sleeve nestled within the housing through bore and having a sleeve bore to hold a plug graft in a shearable orientation aligned within the continuous passageway and oriented to coaxially receive the selected longitudinal cutting blade within the sleeve bore with the blade in close tolerance along an inner bore surface of the holding sleeve to shear the plug graft.

2. The device of claim 1, further comprising an osteochondral plug graft comprising a cartilage layer attached to an underlying body of bone inserted within the plug graft housing for paring by the cutting blade.

3. The device of claim 1, wherein the leading cutting edge is configured in a rectangle, oval, square or circle shape.

4. The device of claim 1, wherein the sleeve bore is configured in a rectangle, oval, square or circle cross sectional shape.

5. The device of claim 1, wherein the holding sleeve includes open slots traverse to the sleeve bore openings that allow a portion of an inserted osteochondral plug graft to impose outwardly from the sleeve bore.

6. The device of claim 1, further comprising an osteochondral plug graft comprising a cartilage layer attached to an underlying body of bone inserted within the plug graft housing and wherein the holding sleeve includes open slots traverse to the sleeve bore that allow a portion of the inserted osteochondral plug graft to impose outwardly from the sleeve bore for paring by the cutting blade.

7. The device of claim 1, wherein the leading cutting edge is configured to pare the plug graft to a cross sectional square shape, rectangular shape, round shape or oval shape.

8. The device of claim 1, wherein:
the housing includes inner surfaces defining a pair of spaced apart receivers each extending parallel to the housing through bore, the housing through bore being positioned between the receivers; and
the impact guide includes a pair of spaced apart vertical guide posts, the vertical guide posts being disposed in the receivers to engage the impact guide with the housing.

9. The device of claim 1, wherein the impact guide includes a slot that horizontally traverses the housing through bore, the blade plate assembly being slidably received in the bore.

10. The device of claim 1, wherein:
the device further comprises a base plate include an opening; and
the housing includes a slot that horizontally traverses the housing through bore, the base plate being slidably received within the slot.

11. The device of claim 10, wherein the device further comprises a support alter including an elongated pedestal, the elongated pedestal being received in the housing through bore such that the support alter is positioned opposite the impactor.

12. The device of claim 11, wherein the elongated pedestal a flat impact surfaces that engages the plug graft or the plug graft holding sleeve when the plug graft holding sleeve is positioned within the housing through bore and the plug graft is positioned within the plug graft holding sleeve.

13. The device of claim 1, wherein the cutting blades each include an extension, the extension of one of the cutting blades interfacing with the lips of a respective opening when the one of the cutting blades is disposed in the respective opening.

14. The device of claim 1, wherein the leading cutting edge is beveled.

15. The device of claim 1, wherein the impactor comprises a cylindrically-shaped body member having a continuous bore formed for receiving the plug graft.

16. The device of claim 15, wherein a cutting slot extends through inner and outer surfaces of the body member such that the cutting slot is in communication with the continuous bore in the body member.

17. The device of claim 16, wherein:
the cuttings slot extends parallel to an axis defined by the impactor; and
the impactor includes indicia on opposite sides of the cutting slot that indicate a distance along the cutting slot.

18. The device of claim 15, wherein:
the body member includes a flange having a circumferential groove; and
the device further comprises a mechanism for adjusting a position of the plug graft comprising:
a rod adapted to extend within the continuous bore in the body member,
and a knob engaged with the rod, the knob including a transverse opening,
and the device includes a dowel that extends through the transverse opening in the rod and into the circumferential groove to engage the knob with the body member.

19. The device of claim 1, wherein the rod threadably engages the knob.

* * * * *